United States Patent
Baba et al.

(10) Patent No.: US 11,479,958 B2
(45) Date of Patent: *Oct. 25, 2022

(54) SANITARY WASHING DEVICE

(71) Applicant: TOTO LTD., Kitakyushu (JP)

(72) Inventors: Kazuma Baba, Kitakyushu (JP);
Toshinari Yaoka, Kitakyushu (JP);
Keisuke Tashiro, Kitakyushu (JP);
Satoru Matsumoto, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 64 days.

This patent is subject to a terminal disclaimer.

(21) Appl. No.: 17/098,877

(22) Filed: Nov. 16, 2020

(65) Prior Publication Data
US 2021/0164212 A1    Jun. 3, 2021

(30) Foreign Application Priority Data

Nov. 29, 2019   (JP) .............................. JP2019-217494

(51) Int. Cl.
*E03D 9/08*   (2006.01)
*A61L 2/08*   (2006.01)

(52) U.S. Cl.
CPC . *E03D 9/08* (2013.01); *A61L 2/08* (2013.01)

(58) Field of Classification Search
CPC ....................................................... E03D 9/08
USPC .............. 4/420.4, 420, 447, 448, 422, 420.5
See application file for complete search history.

(56) References Cited

U.S. PATENT DOCUMENTS

| | | | |
|---|---|---|---|
| 8,856,979 B2 * | 10/2014 | Matsumoto | E03D 9/08 4/443 |
| 10,450,734 B2 * | 10/2019 | Tsujita | A47K 13/24 |
| 10,465,367 B2 * | 11/2019 | Ogawa | E03D 9/08 |
| 10,501,922 B2 * | 12/2019 | Yaoka | B05B 15/70 |
| 10,538,904 B2 * | 1/2020 | Tsujita | A47K 13/26 |
| 10,605,906 B2 * | 3/2020 | Todoroki | E03D 5/105 |
| 10,662,633 B2 * | 5/2020 | Morioka | E03D 9/08 |
| 10,694,907 B2 * | 6/2020 | Tsujita | G01S 13/08 |
| 10,697,165 B2 * | 6/2020 | Morioka | E03D 9/08 |
| 10,724,221 B2 * | 7/2020 | Yoshida | E03D 9/08 |

(Continued)

FOREIGN PATENT DOCUMENTS

| | | |
|---|---|---|
| CN | 103041413 A | 4/2013 |
| JP | 2006-274641 A | 10/2006 |

(Continued)

*Primary Examiner* — Lori L Baker
(74) *Attorney, Agent, or Firm* — Pearne & Gordon LLP

(57) ABSTRACT

A sanitary washing device includes a nozzle, a casing, an illuminator, and a controller. The nozzle discharges water toward a private part of a user in a state of the nozzle is advanced into a toilet. The casing includes a nozzle storage part configured to store an entirety of the nozzle in a state of the nozzle is retracted. The illuminator irradiates sterilizing light into the nozzle storage part. The sterilizing light has a sterilizing action. The controller controls the illuminator. The controller includes a first irradiation mode of causing sterilizing light irradiated from the illuminator to be irradiated toward an outer circumferential surface of the nozzle. The controller includes a second irradiation mode of causing sterilizing light irradiated from the same illuminator as the first irradiation mode to be irradiated toward an inner wall of the nozzle storage part.

5 Claims, 10 Drawing Sheets

(56) References Cited

U.S. PATENT DOCUMENTS

| | | | |
|---|---|---|---|
| 10,731,325 B2* | 8/2020 | Tanogashira | G01S 13/88 |
| 10,736,474 B2* | 8/2020 | Takaki | G01G 19/414 |
| 10,851,533 B2* | 12/2020 | Yaoka | A61L 2/084 |
| 10,907,334 B2* | 2/2021 | Yaoka | A47K 7/08 |
| 11,008,746 B2* | 5/2021 | Ko | B05B 1/20 |
| 11,214,950 B2* | 1/2022 | Yamamura | A47K 13/302 |
| 11,214,951 B2* | 1/2022 | Yamamura | F24H 1/10 |
| 11,220,812 B2* | 1/2022 | Yamamura | E03D 9/08 |
| 2019/0368180 A1* | 12/2019 | Yaoka | E03D 9/08 |
| 2021/0164212 A1* | 6/2021 | Baba | E03D 9/08 |

FOREIGN PATENT DOCUMENTS

| | | |
|---|---|---|
| JP | 2010-189849 A | 9/2010 |
| JP | 2013-083141 A | 5/2013 |
| KR | 10-2013-0039506 A | 4/2013 |

\* cited by examiner

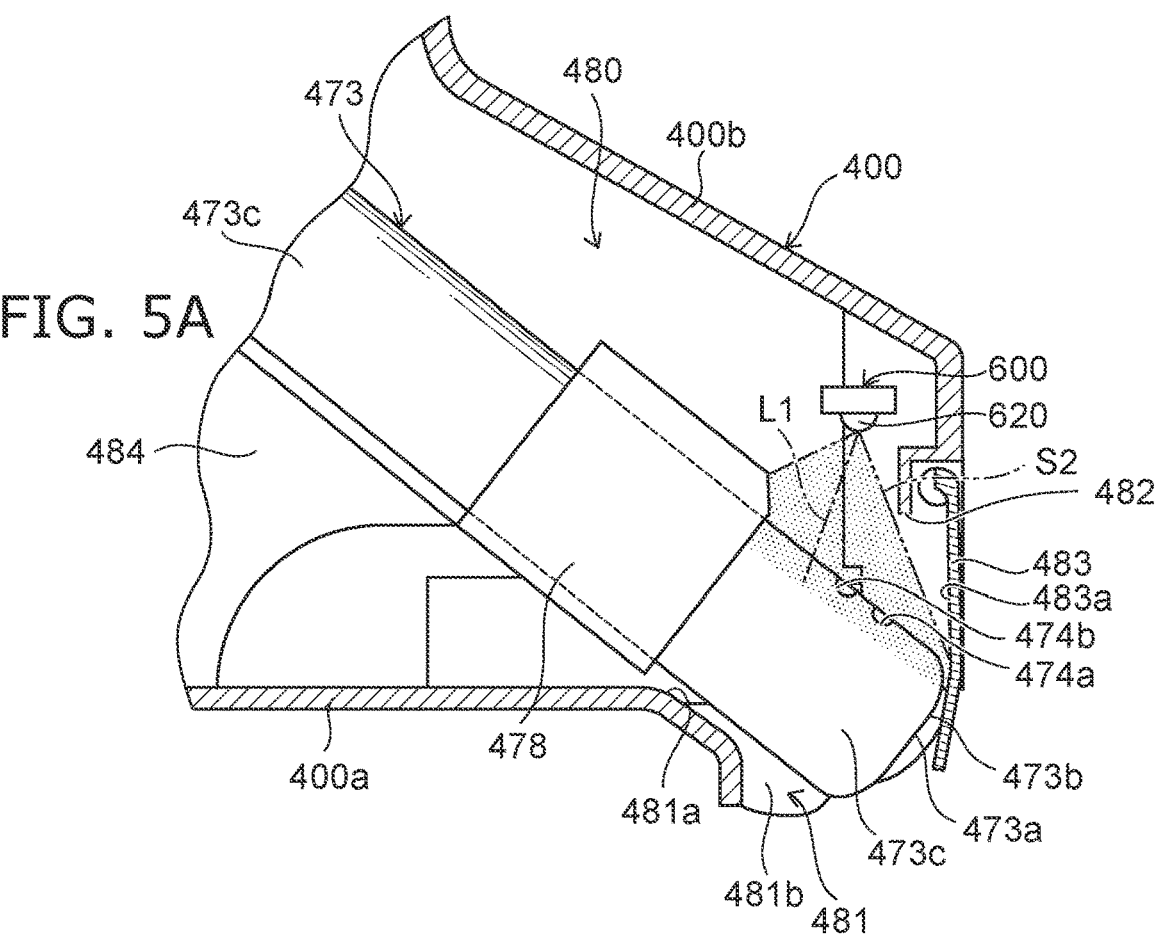
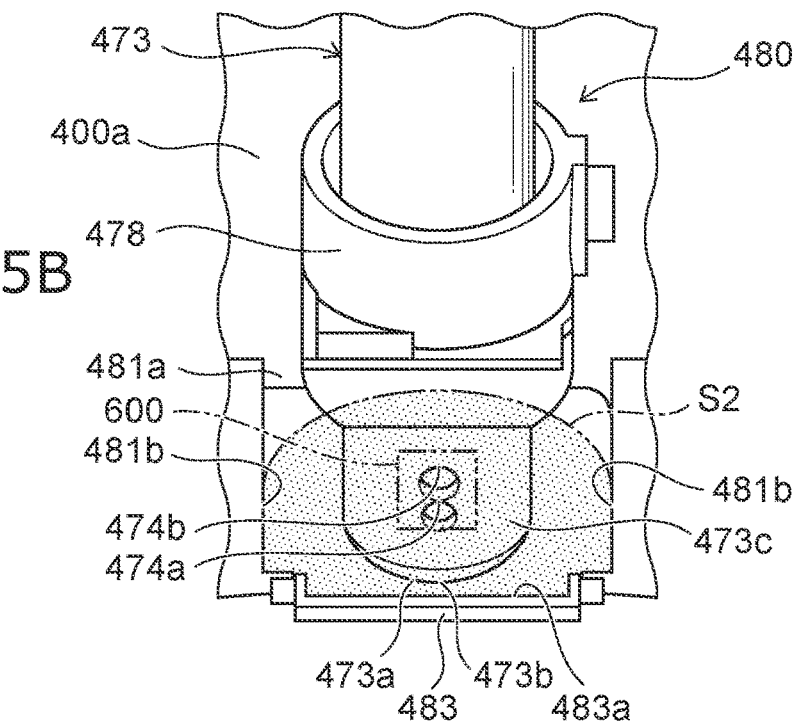

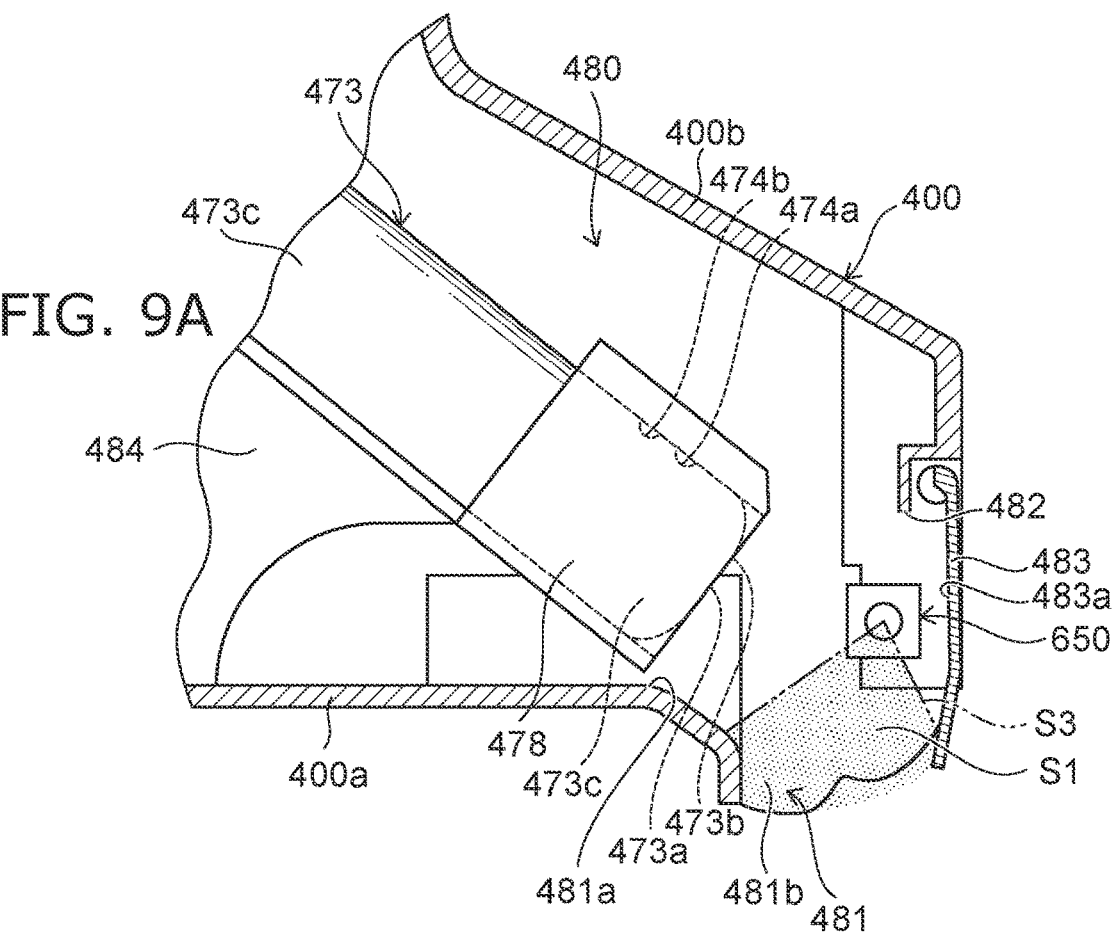
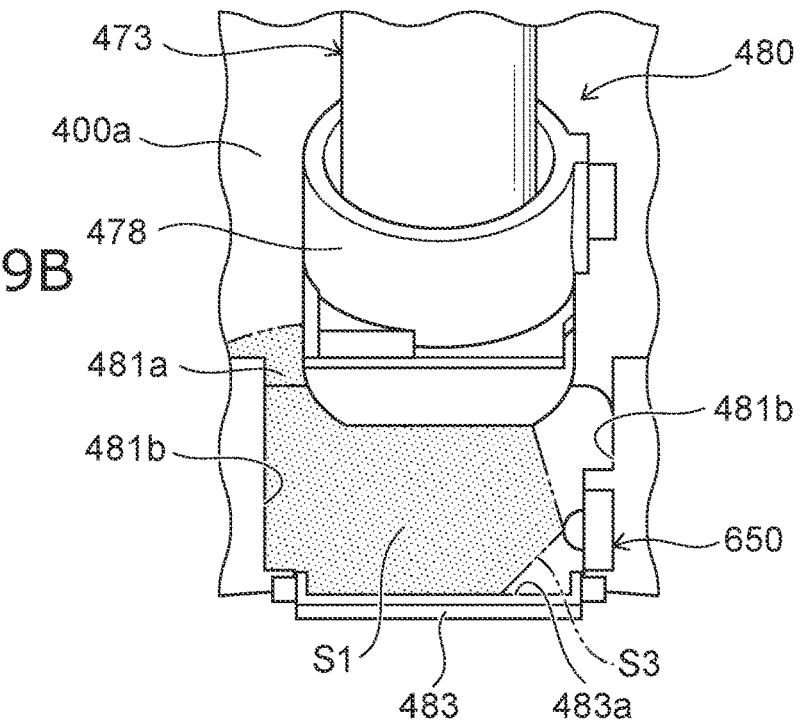

SANITARY WASHING DEVICE

CROSS-REFERENCE TO RELATED APPLICATIONS

This application is based upon and claims the benefit of priority from Japanese Patent Application No. 2019-217494, filed on Nov. 29, 2019; the entire contents of which are incorporated herein by reference.

FIELD

Embodiments described herein relate generally to a sanitary washing device.

BACKGROUND

JP-A 2013-83141 (Kokai) discusses a sanitary washing device including a private part washing nozzle. To remove dirt adhered to the private part washing nozzle in the sanitary washing device, sterilizing water (bacteria removing water) is squirted toward the private part washing nozzle, and sterilizing light (ultraviolet light) that has a sterilizing action is irradiated toward the private part washing nozzle.

The concentration of the sterilizing component of the squirted sterilizing water decreases over time. There is a risk that bacteria and/or mold may easily occur due to the effects of moisture at locations where the sterilizing water having a reduced sterilizing effect remains.

Accordingly, when sterilizing water remains in the nozzle storage part, it is desirable to suppress the occurrence of bacteria and/or mold by irradiating sterilizing light also toward such locations.

However, because the illuminator recited in JP-A 2013-83141 (Kokai) irradiates the sterilizing light from above the private part washing nozzle, there is a risk that the sterilizing light cannot be irradiated on an inner wall of the nozzle storage part that is in a shadow of the private part washing nozzle. Therefore, there is a risk that the sterilizing light recited in JP-A 2013-83141 (Kokai) cannot sufficiently suppress the propagation of bacteria and/or mold occurring in the nozzle storage part.

To solve this problem, it may be considered to separately provide an illuminator to irradiate sterilizing light on the inner wall of the nozzle storage part. However, there is a risk that the cost may increase when multiple light sources are used to generate the sterilizing light. Also, because space must be sufficient to provide the multiple illuminators at the periphery of the nozzle storage part, there is a risk that the casing that stores the private part washing nozzle may become large.

SUMMARY

According to the embodiment, a sanitary washing device includes a private part washing nozzle, a casing, an illuminator, and a controller. The private part washing nozzle discharges water toward a private part of a user in a state of the private part washing nozzle is advanced into a toilet. The casing includes a nozzle storage part configured to store an entirety of the private part washing nozzle in a state of the private part washing nozzle is retracted. The illuminator irradiates sterilizing light into the nozzle storage part. The sterilizing light has a sterilizing action. The controller controls the illuminator. The controller includes a first irradiation mode of causing sterilizing light irradiated from the illuminator to be irradiated toward an outer circumferential surface of the private part washing nozzle. The controller includes a second irradiation mode of causing sterilizing light irradiated from the same illuminator as the first irradiation mode to be irradiated toward an inner wall of the nozzle storage part.

BRIEF DESCRIPTION OF THE DRAWINGS

FIGS. 5A and 5B are explanatory drawings when the first irradiation mode is performed.

FIGS. 9A and 9B are explanatory drawings illustrating the second irradiation mode of the illuminator according to the first modification.

DETAILED DESCRIPTION

Figure 1:
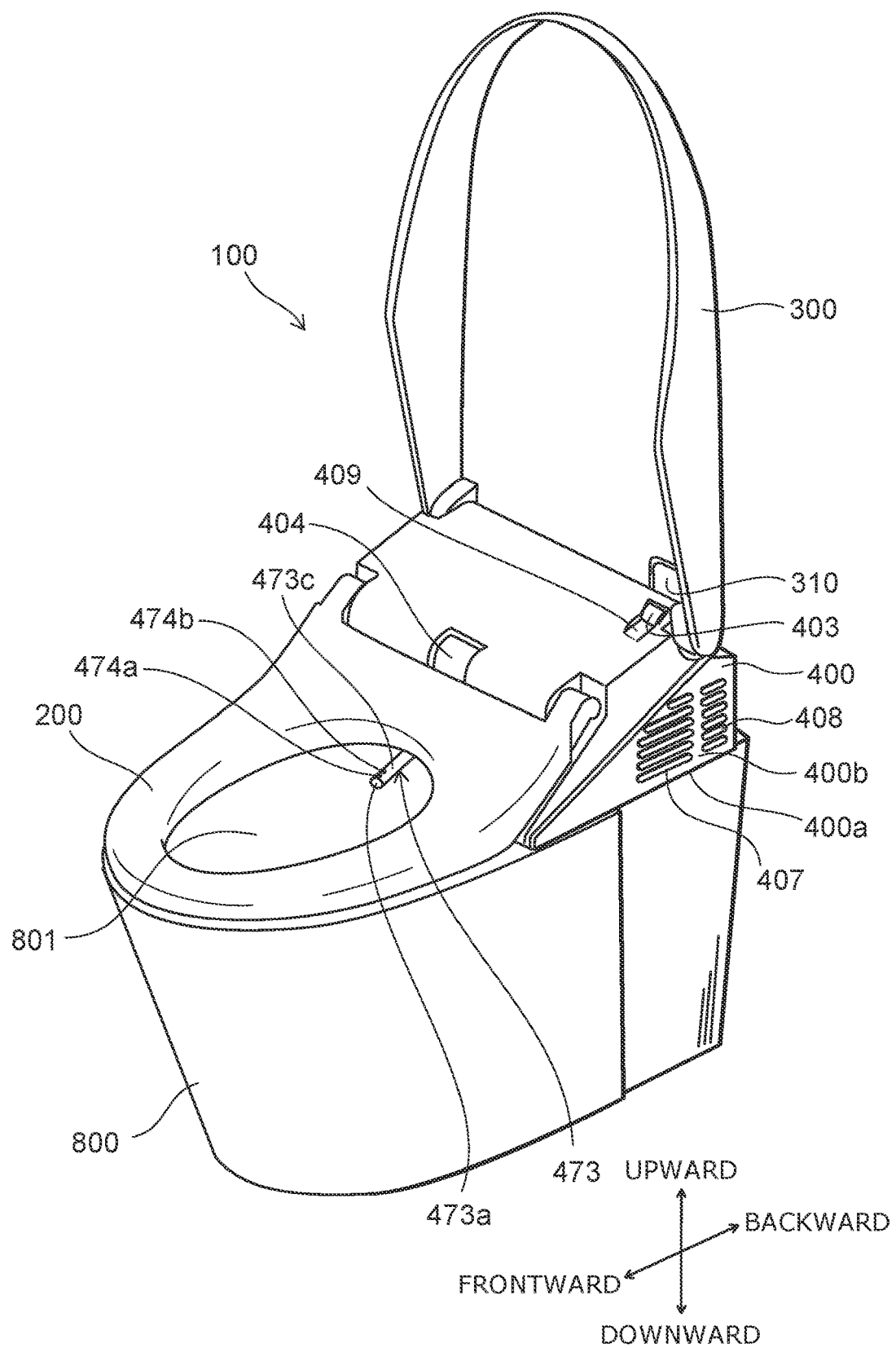
FIG. 1 is a perspective view illustrating a toilet device including a sanitary washing device according to the embodiment.

According to one embodiment, a sanitary washing device including a private part washing nozzle having a water discharge port discharging water toward a private part of a user in a state of the private part washing nozzle being advanced into a toilet, a casing including a nozzle storage part configured to store an entirety of the private part washing nozzle in a state of the private part washing nozzle being retracted, an illuminator irradiating sterilizing light, which has a sterilizing action, into the nozzle storage part, and a controller controlling the illuminator, wherein the controller includes a first irradiation mode of causing sterilizing light irradiated from the illuminator to be irradiated toward an outer circumferential surface of the private part washing nozzle and a second irradiation mode of causing the same sterilizing light as the sterilizing light irradiated from the illuminator in the first irradiation mode to be irradiated toward the inner wall of the nozzle storage part.

According to the sanitary washing device, the sterilizing light can be irradiated on the nozzle storage part and the outer circumferential surface of the private part washing nozzle from the same illuminator. Also, the enlargement of the casing can be suppressed because multiple illuminators may not be provided to sterilize both the private part washing nozzle and the nozzle storage part.

Embodiments of the invention will now be described with reference to the drawings. Similar components in the drawings are marked with the same reference numerals, and a detailed description is omitted as appropriate.

FIG. 1 is a perspective view illustrating a toilet device including a sanitary washing device according to the embodiment.

As illustrated in FIG. 1, the toilet device includes a sit-down flush toilet (for convenience of description hereinbelow, called simply the "toilet") 800 and a sanitary washing device 100 provided at the upper part of the toilet 800. The sanitary washing device 100 includes a casing 400, a toilet seat 200, and a toilet lid 300. The toilet seat 200 and the toilet lid 300 each are pivotally supported to be openable and closable with respect to the casing 400.

A private part washing functional unit that realizes the washing of a private part such as the "bottom" or the like of a user sitting on the toilet seat 200 and the like are provided inside the casing 400. For example, a seating detection sensor 404 that detects the user being seated on the toilet seat 200 is provided in the casing 400. When the seating detection sensor 404 detects the user sitting on the toilet seat 200, a private part washing nozzle (for convenience of description hereinbelow, called simply the "nozzle") 473 can be caused to advance into the toilet 800 (into a bowl 801) or retract from the interior of the bowl 801 when the user operates an operation part 500 such as, for example, a remote control, etc. (referring to FIG. 2). A state in which the nozzle 473 is advanced into the bowl 801 is illustrated in the sanitary washing device 100 illustrated in FIG. 1.

The nozzle 473 washes the human body private part by discharging water toward the human body private part. A bidet wash water discharge port 474a and a bottom wash water discharge port 474b are provided in the tip portion of the nozzle 473. The nozzle 473 can wash a female private part of a female sitting on the toilet seat 200 by squirting water from the bidet wash water discharge port 474a provided in the tip of the nozzle 473. The nozzle 473 also can wash the "bottom" of the user sitting on the toilet seat 200 by squirting water from the bottom wash water discharge port 474b provided in the tip of the nozzle 473. In this specification, "water" includes not only cold water but also warm water that is heated.

The modes of washing the "bottom" include, for example, a "bottom wash" and a "gentle wash" that gently washes using a water stream that is softer than that of the "bottom wash". For example, the nozzle 473 can perform the "bidet wash", the "bottom wash", and the "gentle wash".

Although the bidet wash water discharge port 474a is provided further toward the tip side of the nozzle 473 than the bottom wash water discharge port 474b in the nozzle 473 illustrated in FIG. 1, the mounting positions of the bidet wash water discharge port 474a and the bottom wash water discharge port 474b are not limited to the example. The bidet wash water discharge port 474a may be provided further toward the back end side of the nozzle 473 than the bottom wash water discharge port 474b. Although two water discharge ports are provided in the nozzle 473 illustrated in FIG. 1, three or more water discharge ports may be provided.

Figure 2:
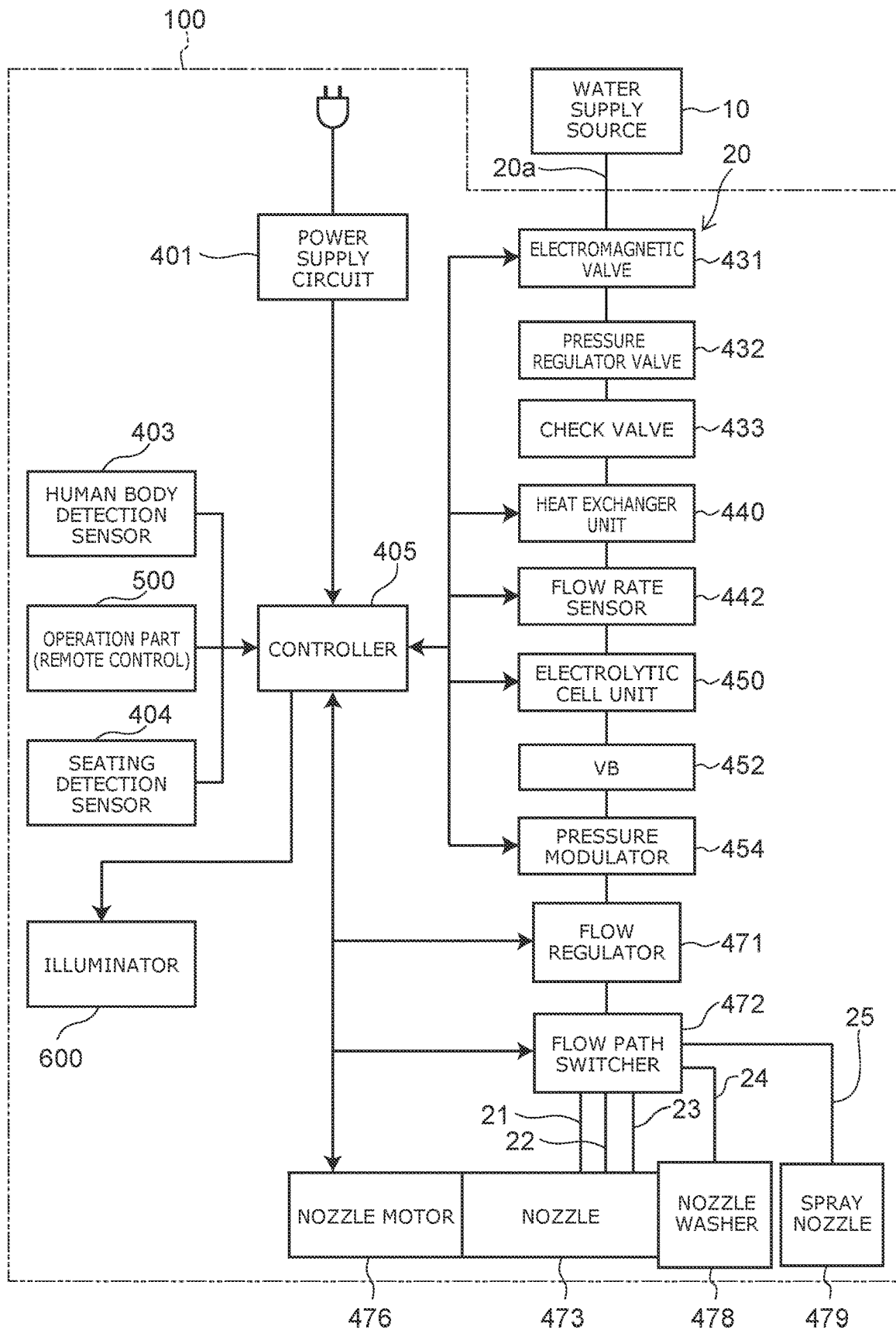
FIG. 2 is a block diagram illustrating the relevant components of the sanitary washing device.

FIG. 2 is a block diagram illustrating the relevant components of the sanitary washing device.

The relevant components of the water channel system and the electrical system are illustrated together in FIG. 2.

As illustrated in FIG. 2, the sanitary washing device 100 includes a water transfer part 20. The water transfer part 20 includes a pipe line 20a that reaches the nozzle 473 from a water supply source 10 such as a service water line, a water storage tank, etc. The water transfer part 20 guides the water supplied from the water supply source 10 to the nozzle 473 via the pipe line 20a. For example, the pipe line 20a is formed of components such as an electromagnetic valve 431, a heat exchanger unit 440, a flow path switcher 472, etc., which are described below, and multiple piping that connects these components.

The electromagnetic valve 431 is provided at the upstream side of the water transfer part 20. The electromagnetic valve 431 is an openable and closeable electromagnetic valve and controls the supply of the water based on a command from a controller 405 provided inside the casing 400. In other words, the electromagnetic valve 431 opens and closes the pipe line 20a. The water that is supplied from the water supply source 10 is caused to flow in the pipe line 20a by setting the electromagnetic valve 431 to the open state.

A pressure regulator valve 432 is provided downstream of the electromagnetic valve 431. The pressure regulator valve 432 regulates the pressure inside the pipe line 20a to be in a prescribed pressure range when the water supply pressure is high. A check valve 433 is provided downstream of the pressure regulator valve 432. The check valve 433 suppresses the backflow of water toward the upstream side of the check valve 433 when the pressure inside the pipe line 20a decreases, etc.

The heat exchanger unit 440 (the heater) is provided downstream of the check valve 433. The heat exchanger unit 440 includes a heater and heats the water supplied from the water supply source 10 to, for example, a specified temperature. In other words, the heat exchanger unit 440 produces warm water.

The heat exchanger unit 440 is, for example, an instant heating-type (instantaneous-type) heat exchanger that uses a ceramic heater, etc. Compared to a warm water storage heating-type heat exchanger that uses a warm water storage tank, the instant heating-type heat exchanger can heat the water to the specified temperature in a short period of time. The heat exchanger unit 440 is not limited to an instant heating-type heat exchanger and may be a warm water storage heating-type heat exchanger. The heater is not limited to a heat exchanger; for example, another heating technique such as one that utilizes microwave heating, etc., may be used.

The heat exchanger unit 440 is connected to the controller 405. For example, the controller 405 heats the water to the temperature set by the operation part 500 by controlling the heat exchanger unit 440 according to an operation of the operation part 500 by the user.

A flow rate sensor 442 is provided downstream of the heat exchanger unit 440. The flow rate sensor 442 detects the flow rate of the water discharged from the heat exchanger unit 440. In other words, the flow rate sensor 442 detects the flow rate of the water flowing through the pipe line 20a. The flow rate sensor 442 is connected to the controller 405. The flow rate sensor 442 inputs the detection result of the flow rate to the controller 405.

An electrolytic cell unit 450 is provided downstream of the flow rate sensor 442. The electrolytic cell unit 450 generates a liquid (functional water) including hypochlorous acid from the service water by electrolyzing the service water flowing through the interior of the electrolytic cell unit 450. The electrolytic cell unit 450 is connected to the controller 405. The electrolytic cell unit 450 generates the sterilizing water (the functional water) based on a control by the controller 405. The electrolytic cell unit 450 is included in the sterilizing water generator of the invention.

The functional water that is generated by the electrolytic cell unit 450 may be, for example, a solution including metal ions such as silver ions, copper ions, etc. Or, the functional water that is generated by the electrolytic cell unit 450 may be a solution including electrolytic chlorine, ozone, etc. Or, the functional water that is generated by the electrolytic cell unit 450 may be acidic water or alkaline water.

A vacuum breaker (VB) 452 is provided downstream of the electrolytic cell unit 450. The vacuum breaker 452 includes, for example, a flow channel for allowing the water to flow, an intake port for intaking air into the flow channel, and a valve mechanism that opens and closes the intake port. For example, the valve mechanism blocks the intake port when water is flowing in the flow channel and intakes air into the flow channel by opening the intake port when the flow of the water stops. In other words, the vacuum breaker 452 intakes air into the pipe line 20*a* when the water does not flow in the water transfer part 20. The valve mechanism includes, for example, a float valve.

As described above, the vacuum breaker 452 intakes air into the pipe line 20*a*, thereby promoting, for example, water drainage of the portion of the pipe line 20*a* downstream of the vacuum breaker 452. For example, the vacuum breaker 452 promotes the water drainage of the nozzle 473. Thus, the vacuum breaker 452 drains the water inside the nozzle 473 and intakes air into the nozzle 473, thereby suppressing, for example, the undesirable backflow toward the water supply source 10 (the fresh water) side of the wash water inside the nozzle 473, the liquid waste collected inside the bowl 801, etc.

A pressure modulator 454 is provided downstream of the vacuum breaker 452. The pressure modulator 454 applies a pulsatory motion to the water discharged from the bidet wash water discharge port 474*a* and the bottom wash water discharge port 474*b* of the nozzle 473 and/or the water discharger of the nozzle washer 478 by applying a pulsatory motion or an acceleration to the flow of the water inside the pipe line 20*a* of the water transfer part 20. In other words, the pressure modulator 454 causes the fluidic state of the water flowing through the pipe line 20*a* to fluctuate. The pressure modulator 454 is connected to the controller 405. The pressure modulator 454 causes the fluidic state of the water to fluctuate based on a control by the controller 405. The pressure modulator 454 causes the pressure of the water inside the pipe line 20*a* to fluctuate.

A flow regulator 471 is provided downstream of the pressure modulator 454. The flow regulator 471 regulates the water force (the flow rate). The flow path switcher 472 is provided downstream of the flow regulator 471. The flow path switcher 472 performs opening and closing and switching of the water supply to the nozzle 473 and/or the nozzle washer 478. The flow regulator 471 and the flow path switcher 472 may be provided as one unit. The flow regulator 471 and the flow path switcher 472 are connected to the controller 405. The operations of the flow regulator 471 and the flow path switcher 472 are controlled by the controller 405.

The nozzle 473, the nozzle washer 478, and the spray nozzle 479 are provided downstream of the flow path switcher 472. The nozzle 473 receives a drive force from the nozzle motor 476, advances into the bowl 801 of the toilet 800, and retracts from the interior of the bowl 801. The nozzle motor 476 is included in the nozzle driver of the invention and causes the nozzle 473 to advance or retract based on a command from the controller 405.

The nozzle washer 478 washes and sterilizes an outer circumferential surface 473*c* (the central body) of the nozzle 473 by squirting sterilizing water (functional water) from the water discharger. The nozzle washer 478 may wash the outer circumferential surface 473*c* of the nozzle 473 by squirting water from the water discharger. The spray nozzle 479 sprays the water or the functional water into the bowl 801 in a mist form. In the example, the spray nozzle 479 is provided separately from the nozzle 473 for washing the human body. The spraying is not limited thereto; a water discharge port for spraying a mist-like liquid into the bowl 801 may be provided in the nozzle 473.

A bottom wash channel 21, a gentle wash channel 22, and a bidet wash channel 23 also are provided downstream of the flow path switcher 472. The bottom wash channel 21 and the gentle wash channel 22 guide, toward the bottom wash water discharge port 474*b*, the water supplied from the water supply source 10 or the functional water generated by the electrolytic cell unit 450 via the water transfer part 20. The bidet wash channel 23 guides, toward the bidet wash water discharge port 474*a*, the water supplied from the water supply source 10 or the functional water generated by the electrolytic cell unit 450 via the water transfer part 20.

A surface wash channel 24 and a spray channel 25 also are provided downstream of the flow path switcher 472. The surface wash channel 24 guides, toward the nozzle washer 478, the water supplied from the water supply source 10 or the functional water generated by the electrolytic cell unit 450 via the water transfer part 20. The spray channel 25 guides, toward the spray nozzle 479, the water supplied from the water supply source 10 or the functional water generated by the electrolytic cell unit 450 via the water transfer part 20.

By controlling the flow path switcher 472, the controller 405 switches the opening and closing of the flow channels of the bottom wash channel 21, the gentle wash channel 22, the bidet wash channel 23, the surface wash channel 24, and the spray channel 25. Thus, the flow path switcher 472 switches between the state of communicating with the pipe line 20*a* and the state of not communicating with the pipe line 20*a* for each of the multiple water discharge ports of the bidet wash water discharge port 474*a*, the bottom wash water discharge port 474*b*, the nozzle washer 478, the spray nozzle 479, etc.

The controller 405 is supplied with electrical power from a power supply circuit 401 and controls the operations of the electromagnetic valve 431, the heat exchanger unit 440, the electrolytic cell unit 450, the pressure modulator 454, the flow regulator 471, the flow path switcher 472, the nozzle motor 476, etc., based on signals from a human body detection sensor 403, the seating detection sensor 404, the flow rate sensor 442, the operation part 500, etc For example, the controller 405 also controls an illuminator 600 based on detection information of the human body detection sensor 403 and/or the seating detection sensor 404. The illuminator 600 irradiates sterilizing light, which is light having a sterilizing action, on the periphery of the nozzle 473 (a nozzle storage part 480 described below, etc.). The controller 405 includes a first irradiation mode of causing the sterilizing light irradiated from the illuminator 600 to be irradiated toward the outer circumferential surface 473*c* of the nozzle 473, and a second irradiation mode of causing sterilizing light irradiated from the same illuminator 600 as the first irradiation mode to be irradiated toward an inner wall 481 of the nozzle storage part 480. The controller 405 also includes a sterilizing water mode of sterilizing the nozzle 473 by using sterilizing water supplied from the electrolytic cell unit 450. The first irradiation mode, the second irradiation mode, and the sterilizing water mode are described below.

As illustrated in FIG. 1, the human body detection sensor 403 is sunk into a recessed portion 409 formed in the upper surface of the casing 400 and detects the user (the human body) approaching the toilet seat 200. In other words, the human body detection sensor 403 detects the user at the vicinity of the sanitary washing device 100. A transmissive window 310 is provided at the back part of the toilet lid 300. Therefore, the human body detection sensor 403 can detect the existence of the user via the transmissive window 310 in the state in which the toilet lid 300 is closed. For example, the controller 405 responds to the detection of the user by the human body detection sensor 403 by automatically opening the toilet lid 300.

Various mechanisms such as a "deodorizing unit", a "room heating unit", a "warm air drying function" that dries the "bottom" or the like of the user sitting on the toilet seat 200 by blowing warm air toward the "bottom" or the like, etc., also may be provided as appropriate in the casing 400. In such a case, an exhaust port 407 from the deodorizing unit and a vent 408 from the room heating unit are provided as appropriate in the side surface of the casing 400. However, in the invention, the sanitary washing functional units or the other additional functional units may not always be provided.

Figure 3A:
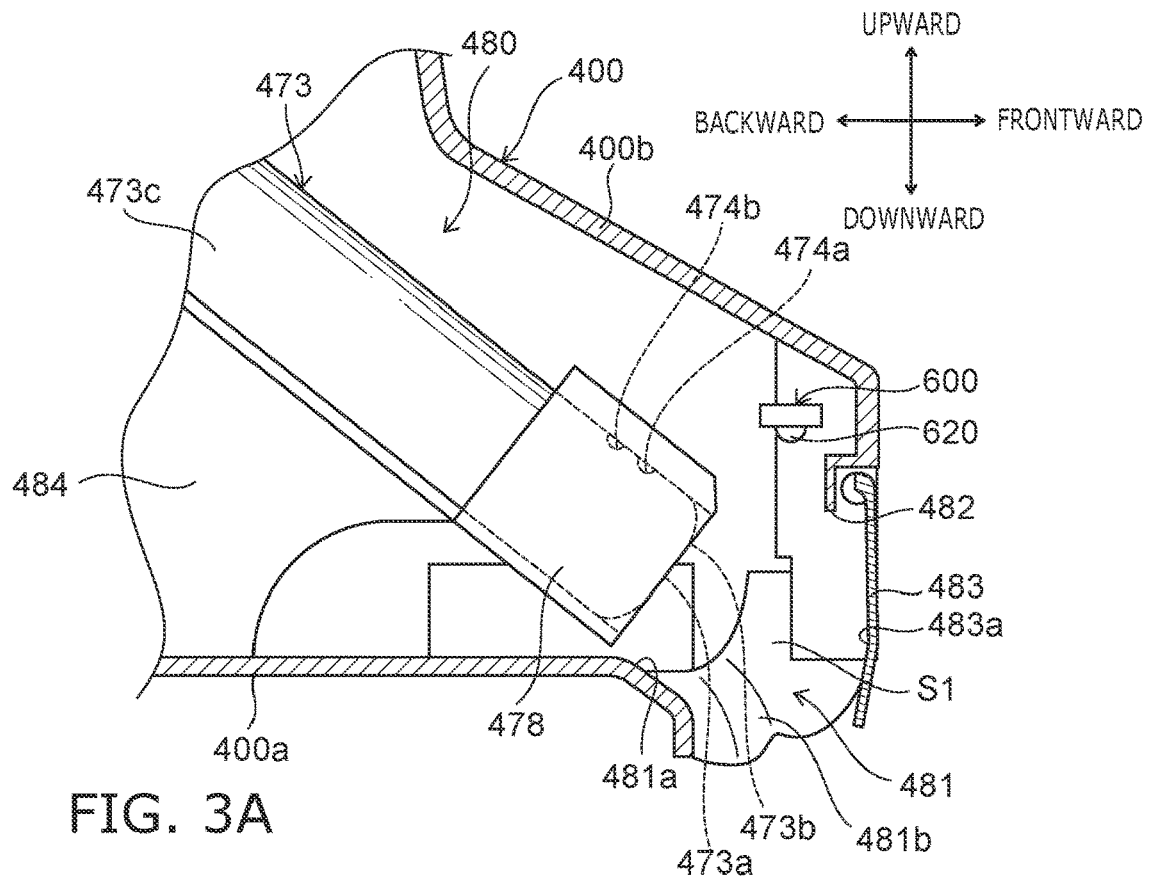
FIGS. 3A and 3B are cross-sectional views of the private part washing nozzle and the nozzle storage part when viewed from the side.
Figure 3B:
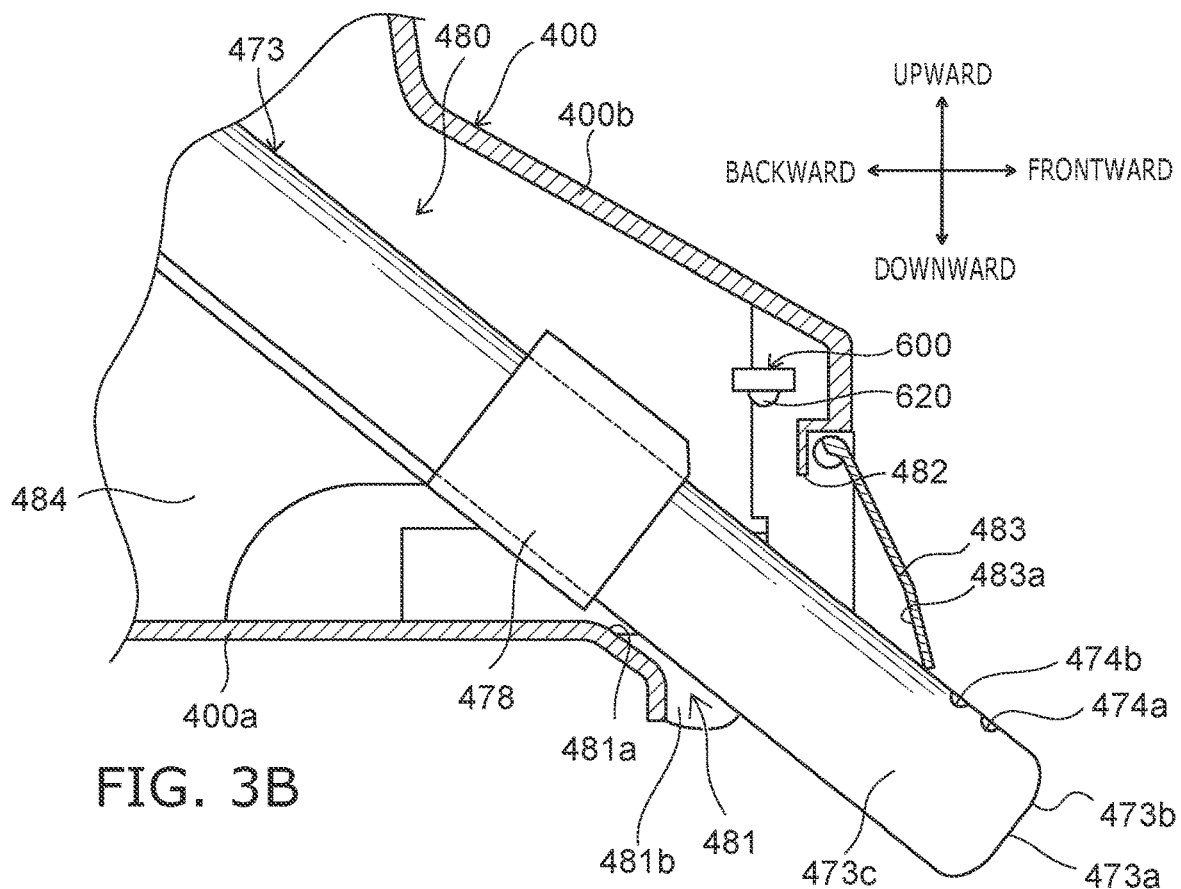

FIGS. 3A and 3B are cross-sectional views of the private part washing nozzle and the nozzle storage part when viewed from the side. FIG. 3A is a cross-sectional view showing a state in which the private part washing nozzle is retracted and stored in the nozzle storage part. FIG. 3B is a cross-sectional view showing a state in which the private part washing nozzle is advanced.

Figure 4:
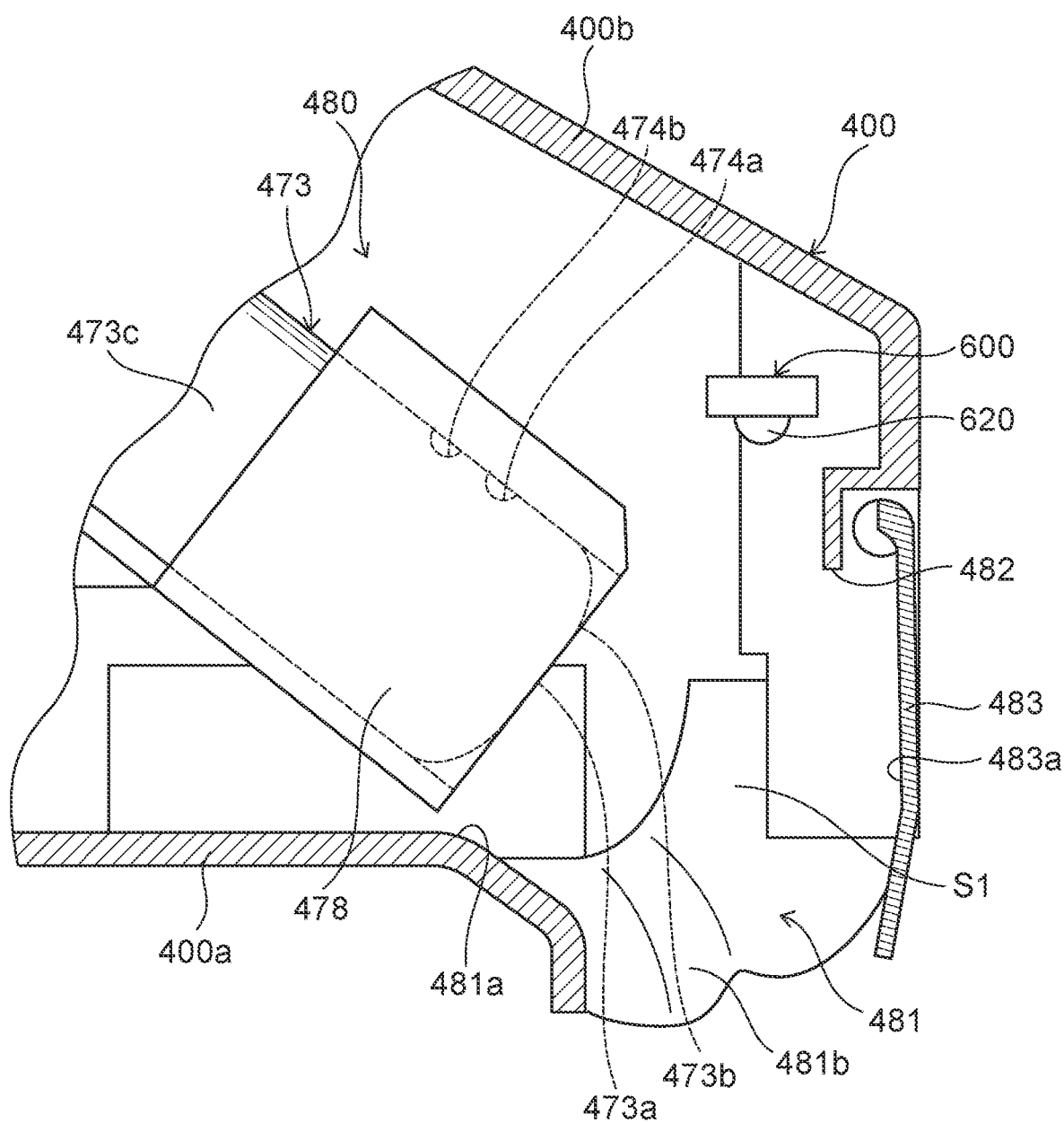
FIG. 4 is an enlarged cross-sectional view of the front end side of the private part washing nozzle in FIG. 3A.

FIG. 4 is an enlarged cross-sectional view of the front end side of the private part washing nozzle in FIG. 3A.

FIGS. 5A and 5B are explanatory drawings when the first irradiation mode is performed. FIG. 5A is a cross-sectional view of the private part washing nozzle and the nozzle storage part when viewed from the side. FIG. 5B is a plan view of the private part washing nozzle and the nozzle storage part when viewed from above.

Figure 6A:
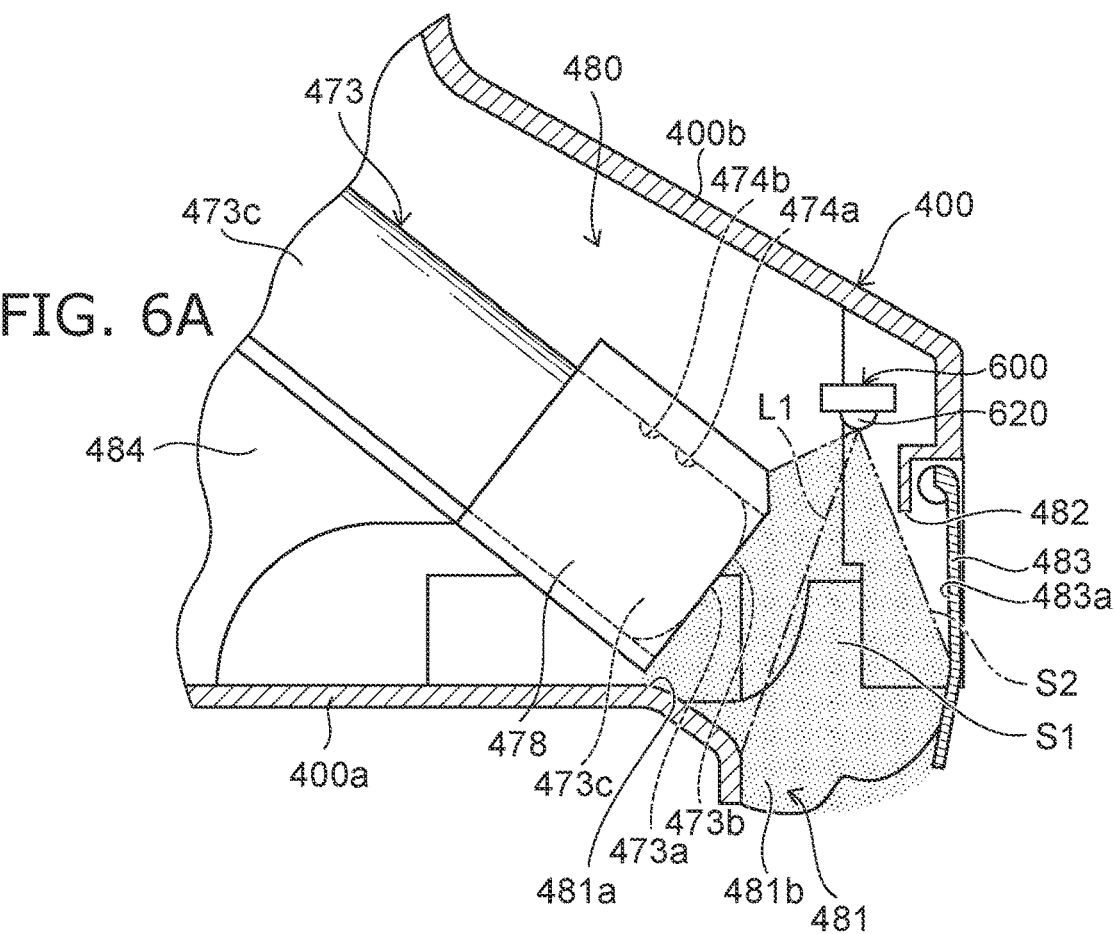
FIGS. 6A and 6B are explanatory drawings when the second irradiation mode is performed.
Figure 6B:
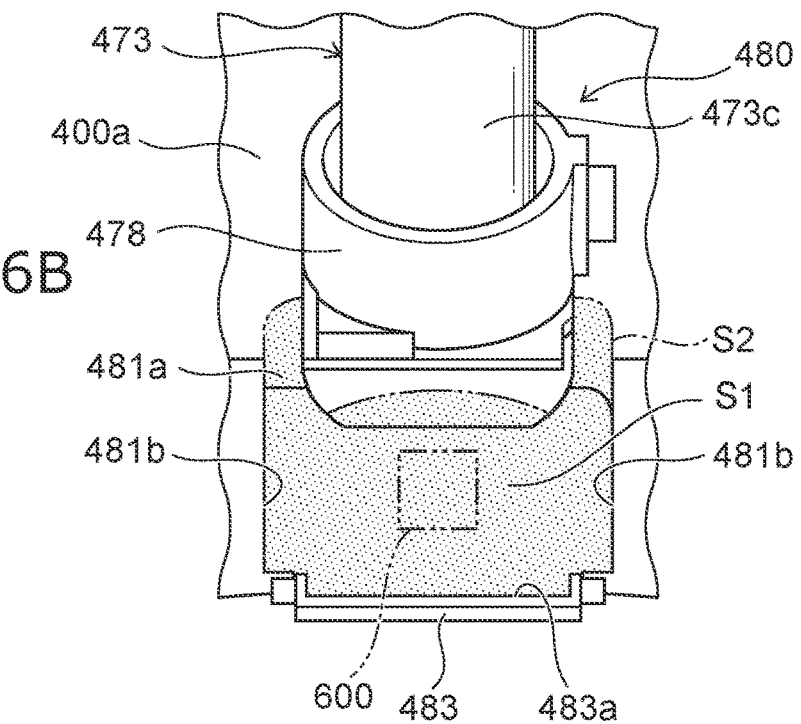

FIGS. 6A and 6B are explanatory drawings when the second irradiation mode is performed. FIG. 6A is a cross-sectional view of the private part washing nozzle and the nozzle storage part when viewed from the side. FIG. 6B is a plan view of the private part washing nozzle and the nozzle storage part when viewed from above.

As illustrated in FIGS. 3A and 4, the casing 400 includes the nozzle storage part 480 that is configured to store the entire nozzle 473 in the state in which the nozzle 473 is retracted. In other words, the nozzle storage part 480 is the portion of the interior of the casing 400 in which the nozzle 473 is stored.

The nozzle storage part 480 includes a nozzle lid 483 that is configured to open and close an opening 482 provided at the front end of the nozzle storage part 480, a bottom portion 481a of a case plate 400a, which forms the bottom surface of the casing 400 positioned below the nozzle 473, and a sidewall part 481b of the case plate 400a positioned at both the left and right sides of the bottom portion 481a. The nozzle lid 483 may not be provided. The inner wall 481 of the nozzle storage part 480 is formed of the bottom portion 481a and the sidewall part 481b. The nozzle storage part 480 is covered with the case cover 400b from above. A nozzle supporter 484 that supports the nozzle 473 to be advanceable and retractable is provided in the nozzle storage part 480.

The bottom portion 481a is tilted into the bowl 801 of the toilet 800. Thereby, the sterilizing water that is discharged from the nozzle washer 478 and the bidet wash water discharge port 474a and/or the bottom wash water discharge port flows down from the bottom portion 481a into the bowl 801 of the toilet 800.

The nozzle supporter 484 supports the nozzle 473 below the nozzle 473. The nozzle supporter 484 is tilted downward along a direction from the back toward the front. The nozzle 473 advances and retracts while sliding with respect to the nozzle supporter 484. For example, a tubular member that stores the nozzle 473 may be provided in the nozzle storage part 480.

The nozzle washer 478 is provided at the tip of the nozzle 473 in the state in which the nozzle 473 is retracted into the casing 400. The nozzle washer 478 includes a water discharger in which a water discharge hole that discharges sterilizing water and water toward the outer circumferential surface 473c of the nozzle 473 is formed. The opening 482 is provided in the front end of the nozzle storage part 480. The opening 482 is provided in the lower side of the front surface of the casing 400. The nozzle washer 478 is positioned backward of the opening 482. For example, the nozzle washer 478 washes the outer circumferential surface 473c (the central body) of the nozzle 473 by squirting sterilizing water and/or water from the water discharger when the nozzle 473 advances and retracts.

The nozzle lid 483 is provided frontward of the nozzle 473. The nozzle lid 483 is pivotally supported by the case cover 400b of the casing 400 and is configured to open and close the opening 482 of the front surface of the case cover 400b provided at the front end of the nozzle storage part 480. The nozzle lid 483 is in an open state in which the opening 482 is open when the nozzle 473 is advanced into the toilet 800, and the nozzle lid 483 is in a closed state in which the opening 482 is closed when the entire nozzle 473 is stored in the nozzle storage part 480.

When the nozzle 473 is not used, the nozzle 473 is stored in the nozzle storage part 480 as illustrated in FIGS. 3A and 4. When the private part wash is performed by the nozzle 473, the nozzle 473 slides frontward and downward with respect to the nozzle storage part 480 as illustrated in FIG. 3B. For example, the nozzle 473 is washed by discharging water from the nozzle washer 478 until the nozzle 473 reaches a prescribed position.

When the nozzle 473 reaches the prescribed position, water is discharged from the bidet wash water discharge port 474a or the bottom wash water discharge port 474b toward the private part of the user, and washing is performed. When the private part wash is completed, the nozzle 473 slides backward and upward toward the nozzle storage part 480. For example, the nozzle 473 is washed and sterilized by the sterilizing water discharged from the nozzle washer 478 until the nozzle 473 is stored in the nozzle storage part 480. In such a case, the sterilizing water that is discharged from the nozzle washer 478 contacts the inner wall 481 of the nozzle storage part 480 and the inner surface of the nozzle lid 483 and flows down into the toilet 800 (into the bowl 801). Accordingly, the sterilizing water also sterilizes the interior of the nozzle storage part 480.

A space S1 is formed between the nozzle 473 and the nozzle lid 483 as illustrated in FIGS. 3A to 4. For example, the space S1 is formed so that the bidet wash water discharge port 474a and the bottom wash water discharge port 474b are exposed outside the nozzle washer 478 before the nozzle 473 contacts the nozzle lid 483 when the nozzle 473 advances. In other words, the nozzle 473 can advance through the nozzle storage part 480 to a position at which the bidet wash water discharge port 474a and the bottom wash water discharge port 474b are outside the nozzle washer 478.

The illuminator 600 irradiates sterilizing light, which has a sterilizing action, into the nozzle storage part 480. As illustrated in FIGS. 3A to 4, for example, the illuminator 600 is positioned inside the casing 400 and is mounted to the case cover 400b. In the example as illustrated in FIGS. 3A to 6B, the illuminator 600 is positioned higher than the nozzle 473 and irradiates the sterilizing light downward from above.

As illustrated in FIG. 4, the illuminator 600 is located further upward and frontward than an upper end 473b of a front surface 473a of the nozzle 473 in the state in which the nozzle 473 is retracted. In other words, the illuminator 600 is located above the space S1 between the nozzle 473 and the nozzle lid 483. Thereby, the illuminator 600 can irradiate the sterilizing light on the outer circumferential surface 473c of the nozzle 473 in the first irradiation mode in which the nozzle 473 is advanced.

In the embodiment, the sterilizing light can be irradiated on the bidet wash water discharge port 474a, the bottom wash water discharge port 474b, and the periphery of the bidet wash water discharge port 474a and the bottom wash water discharge port 474b because the illuminator 600 is positioned above the bidet wash water discharge port 474a and the bottom wash water discharge port 474b of the nozzle 473. On the other hand, the illuminator 600 can irradiate the sterilizing light on the inner wall 481 of the nozzle storage part 480 in the second irradiation mode in which the nozzle 473 is retracted.

At least a portion of the bacteria adhered to the inner wall 481 of the nozzle storage part 480 and the outer circumferential surface 473c of the nozzle 473 is sterilized by being annihilated or deactivated by the irradiation of the sterilizing light. In such a case, for example, it is favorable for the direction (the optical axis) in which the sterilizing light of the illuminator 600 is directed to contact the outer circumferential surface 473c of the nozzle 473 and/or the bidet wash water discharge port 474a or the bottom wash water discharge port 474b in the first irradiation mode. On the other hand, it is favorable for the optical axis to contact the inner wall 481 of the nozzle storage part 480 in the second irradiation mode.

The direction in which the sterilizing light is directed can be considered to be the direction in which the irradiance of the sterilizing light is a maximum. Thereby, the illuminator 600 can effectively sterilize the outer circumferential surface 473c of the nozzle 473 and the inner wall 481 of the nozzle storage part 480. For example, the optical axis at which the irradiance is greatest is the center of the irradiation width of the sterilizing light (the central axis of the divergence angle). There may be multiple optical axes at which the irradiance is greatest when a lens or the like is provided frontward of the illuminator 600.

The illuminator 600 includes, for example, a light-emitting element 620 (a light-emitting body). The light-emitting element 620 is, for example, an LED (Light Emitting Diode). The light-emitting element 620 is not limited to an LED and may be, for example, a LD (Laser Diode), an OLED (Organic Light Emitting Diode), etc. The light-emitting element 620 may be, for example, a cold cathode fluorescent tube or a hot cathode fluorescent tube. The wavelength of the sterilizing light radiated by the light-emitting element 620 is, for example, 250 nm to 480 nm.

The light-emitting element 620 is connected to the controller 405 via a substrate and is lit and unlit based on a control of the controller 405. The controller 405 controls the operation of the illuminator 600 by controlling the light-emitting element 620 to be lit and unlit. The controller 405 also may control the irradiance of the light-emitting element 620 by adjusting the voltage applied to the light-emitting element 620.

The sanitary washing device 100 according to the embodiment has a configuration such as that described above; the sterilizing water mode, the first irradiation mode, and the second irradiation mode that are performed by the controller 405 will now be described.

Figure 7:
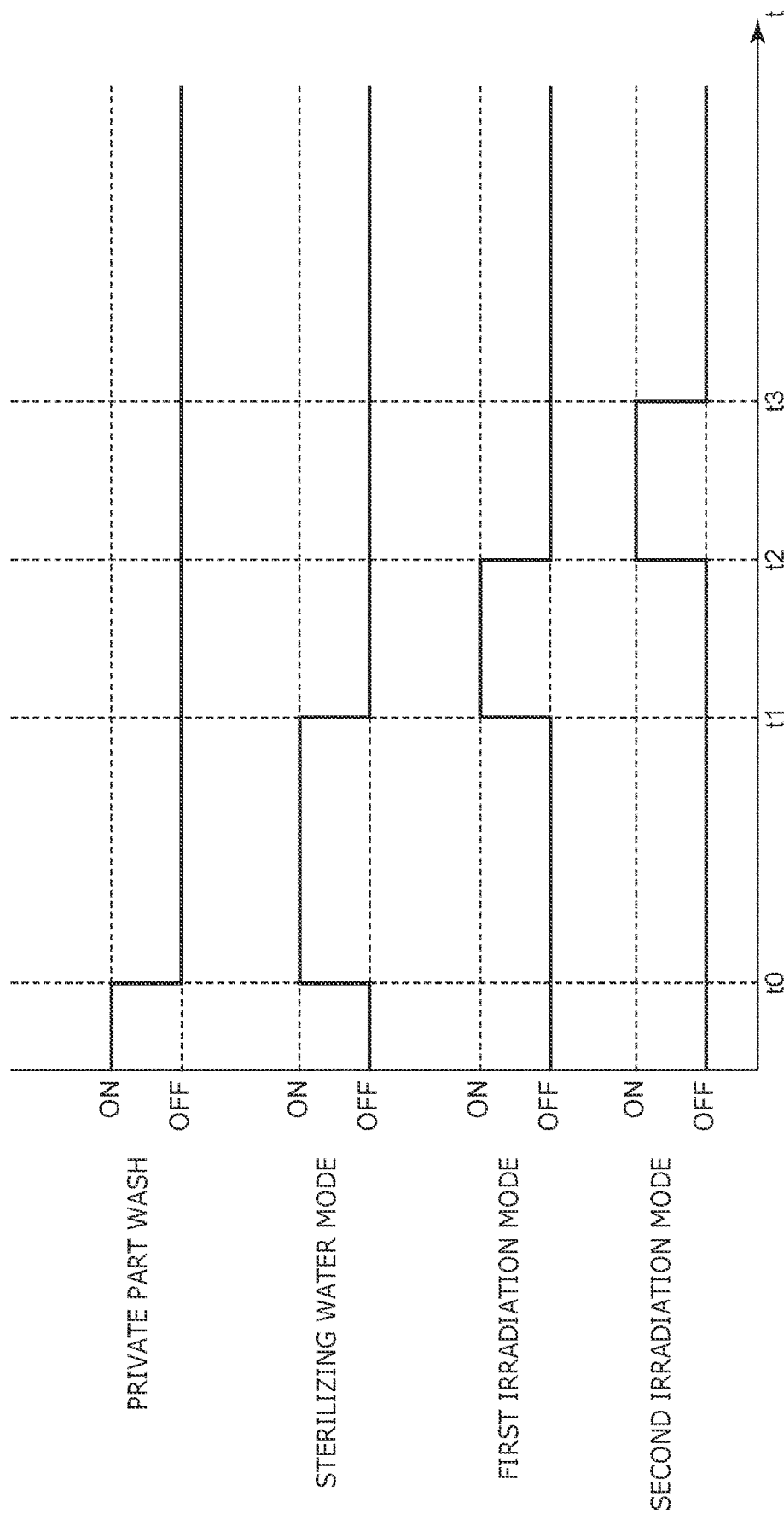
FIG. 7 is an explanatory drawing illustrating an example of the progress states of the sterilizing water mode, the first irradiation mode, and the second irradiation mode.

FIG. 7 is an explanatory drawing illustrating an example of the progress states of the sterilizing water mode, the first irradiation mode, and the second irradiation mode.

For example, when the user that is seated on the toilet seat 200 operates the operation part 500 (the remote control), the nozzle 473 reaches the prescribed position. Subsequently, the private part wash is performed by discharging water from the bidet wash water discharge port 474a or the bottom wash water discharge port 474b toward the private part of the user.

Then, at a time t0, the private part wash is completed (OFF), and the nozzle 473 slides backward and upward toward the nozzle storage part 480. Accordingly, the controller 405 performs the sterilizing water mode (from OFF to ON). In the sterilizing water mode, the outer circumferential surface 473c of the nozzle 473 is washed and sterilized by the sterilizing water discharged from the nozzle washer 478 until the nozzle 473 is stored in the nozzle storage part 480.

After the front end of the nozzle 473 is retracted until the front end of the nozzle 473 is stored inside the nozzle washer 478, the bidet wash water discharge port 474a and the bottom wash water discharge port 474b are washed and sterilized by the sterilizing water discharged from the bidet wash water discharge port 474a and the bottom wash water discharge port 474b of the nozzle 473.

In such a case, the sterilizing water flows through the nozzle storage part 480 and flows down into the toilet 800 (into the bowl 801) from the opening 482. Accordingly, in addition to the nozzle 473, the sterilizing water also sterilizes the inner wall 481 of the nozzle storage part 480 and the inner surface 483a of the nozzle lid 483.

Nearly all of the sterilizing water flowing through the nozzle storage part 480 flows down into the bowl 801 of the toilet 800 from the opening 482. However, for example, there are cases where the sterilizing water remains at the inner wall 481 of the nozzle storage part 480 due to the configuration of the nozzle storage part 480, the surface tension of the sterilizing water, etc. Thus, concentration decay of the remaining sterilizing water progresses over time. Thereby, the interior of the nozzle storage part 480 undesirably becomes an environment in which bacteria and/or mold easily occur.

Here, in the conventional art described above, because the illuminator is located above the nozzle, there is a risk that bacteria and/or mold easily occur because the sterilizing light is not irradiated on the inner wall of the nozzle storage part in the shadow of the nozzle. Also, it may be considered to separately provide an illuminator that irradiates sterilizing light on the inner wall of the nozzle storage part. However, there is a risk that the cost may increase if multiple light sources for generating the sterilizing light are used. Also, there is a risk that the casing that stores the nozzle may become large because space must be sufficient to provide the multiple illuminators at the periphery of the nozzle storage part.

Therefore, in the embodiment, the first irradiation mode and the second irradiation mode are performed after the sterilizing water mode. The controller 405 performs the first and second irradiation modes by using the nozzle motor 476 to change the position of the nozzle 473.

At a time t1 illustrated in FIG. 7, the sterilizing water mode ends (from ON to OFF), and the first irradiation mode is performed (from OFF to ON). The first irradiation mode may be performed after a prescribed period of time has elapsed after the sterilizing water mode has ended. As an example, the first irradiation mode may be performed when the seating detection sensor 404 is switched from ON to OFF.

When the first irradiation mode is performed, the controller 405 causes the nozzle motor 476 to advance the nozzle 473. In such a case as illustrated in FIGS. 5A and 5B, the controller 405 advances the nozzle 473 to a position such that the nozzle lid 483 is not in the open state. In other words, the controller 405 stops the advance of the nozzle 473 before the front end of the nozzle 473 contacts the nozzle lid 483.

Subsequently, the controller 405 causes the illuminator 600 to be lit. Thereby, as in an irradiation area S2 illustrated by double dot-dash lines in FIGS. 5A and 5B, the sterilizing light is irradiated on the outer circumferential surface 473c of the nozzle 473. In such a case, the bidet wash water discharge port 474a and the bottom wash water discharge port 474b of the nozzle 473 are exposed outside the nozzle washer 478. Accordingly, the illuminator 600 can sterilize the front end side of the nozzle 473 by irradiating the sterilizing light on the bidet wash water discharge port 474a and the bottom wash water discharge port 474b of the nozzle 473 and the outer circumferential surface 473c at the periphery of the bidet wash water discharge port 474a and the bottom wash water discharge port 474b.

The sterilizing effect can be improved by directing an optical axis L of the sterilizing light toward the outer circumferential surface 473c of the nozzle 473 and the bidet wash water discharge port 474a and/or the bottom wash water discharge port 474b. In such a case, the advanced position of the nozzle 473 may be changed so that the optical axis L of the sterilizing light contacts the outer circumferential surface 473c of the nozzle 473, the bidet wash water discharge port 474a, and the bottom wash water discharge port 474b.

At a time t2 illustrated in FIG. 7, the first irradiation mode ends (from ON to OFF), and the second irradiation mode is performed (from OFF to ON). When the first irradiation mode ends, the controller 405 causes the illuminator 600 to be unlit. When the second irradiation mode is performed, the controller 405 causes the nozzle motor 476 to retract the nozzle 473.

Here, the illuminator 600 is located above the space S1 between the nozzle 473 and the nozzle lid 483 in the state in which the nozzle 473 is retracted (the state of FIG. 4). Accordingly, as illustrated in FIGS. 6A and 6B, the space below the illuminator 600 is open when the nozzle 473 is retracted. Then, the controller 405 causes the illuminator 600 to be lit. Thereby, as in the irradiation area S2 illustrated by the double dot-dash lines in FIGS. 5A and 5B, the sterilizing light can be irradiated on the inner wall 481 of the nozzle storage part 480, which is in the shadow of the nozzle 473 in the first irradiation mode.

The propagation of bacteria and/or mold due to the remaining sterilizing water can be suppressed by directing the optical axis L of the sterilizing light toward the front end side of the bottom portion 481a where the sterilizing water of the sterilizing water mode easily remains. Accordingly, the illuminator 600 can effectively sterilize the inner wall 481 of the nozzle storage part 480. The illuminator 600 may continuously be in the lit state from when the first irradiation mode ends until the second irradiation mode ends without being unlit when the first irradiation mode ends. Then, at a time t3, the second irradiation mode ends (from ON to OFF).

The controller 405 causes the illuminator 600 to be unlit when the second irradiation mode ends. In the example, the second irradiation mode is performed after the first irradiation mode as an example. However, the invention is not limited thereto; for example, the first irradiation mode may be performed after the second irradiation mode. In other words, the sequence of the first and second irradiation modes can be arbitrarily set.

As a result, in the sanitary washing device according to the embodiment, the nozzle 473 and the nozzle storage part 480 can be sterilized by one illuminator 600. In other words, in the first irradiation mode, the nozzle 473 can be advanced, and the sterilizing light can be irradiated on the outer circumferential surface 473c of the nozzle 473. On the other hand, in the second irradiation mode, the nozzle 473 can be retracted, and the sterilizing light can be irradiated on the inner wall 481 of the nozzle storage part 480, which is in a shadow when the nozzle 473 is advanced.

The controller 405 performs the first and second irradiation modes when the nozzle lid 483 is in the closed state. Thereby, leakage of the sterilizing light outside the casing 400 can be suppressed when the first and second irradiation modes are performed. The first irradiation mode and the second irradiation mode are performed after the sterilizing water mode that uses the sterilizing water to sterilize the nozzle 473; therefore, for example, the sterilizing light can be irradiated on the sterilizing water remaining in the nozzle storage part 480. The propagation of bacteria and/or mold having a risk of occurring due to the residual water of the sterilizing water can be suppressed thereby.

Figure 8A:
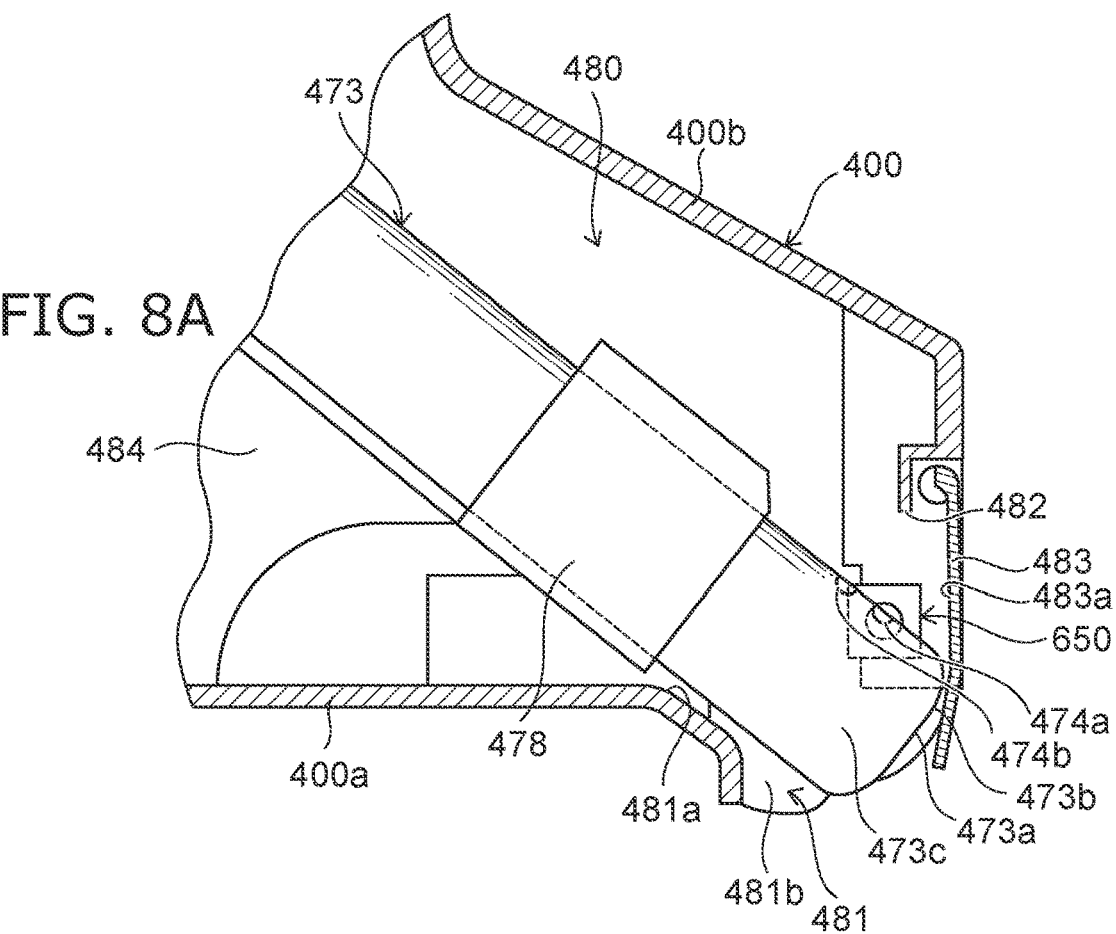
FIGS. 8A and 8B are explanatory drawings illustrating the first irradiation mode of an illuminator according to a first modification.
Figure 8B:
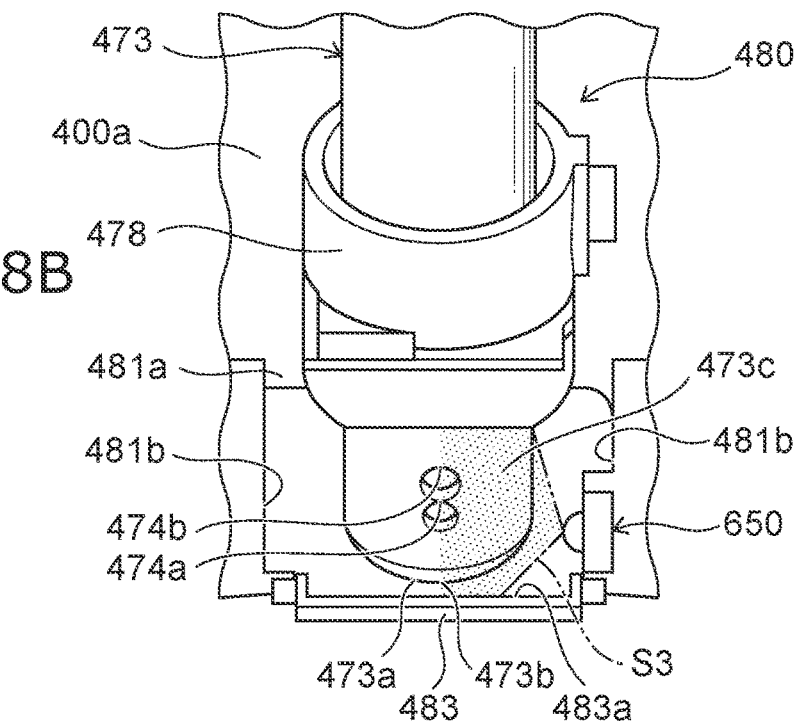

FIGS. 8A and 8B are explanatory drawings illustrating the first irradiation mode of an illuminator according to a first modification. FIG. 8A is a cross-sectional view of the nozzle and the nozzle storage part when viewed from the side. FIG. 8B is a plan view of the nozzle and the nozzle storage part when viewed from above.

FIGS. 9A and 9B are explanatory drawings illustrating the second irradiation mode of the illuminator according to the first modification. FIG. 9A is a cross-sectional view of the nozzle and the nozzle storage part when viewed from the side. FIG. 9B is a plan view of the nozzle and the nozzle storage part when viewed from above.

An example is described in the embodiment described above in which the illuminator 600 is located higher than the nozzle 473. However, the invention is not limited thereto; for example, as in the first modification illustrated in FIG. 8A to FIG. 9B, the illuminator 650 may be located at the side of the nozzle 473.

In such a case, the nozzle 473 is advanced toward the nozzle lid 483 in the first irradiation mode illustrated in FIGS. 8A and 8B. Then, as in the irradiation area S3 illustrated by the double dot-dash lines of FIG. 8B, the sterilizing light is irradiated from the illuminator 650 toward the outer circumferential surface 473c of the nozzle 473. Thereby, the bidet wash water discharge port 474a and the bottom wash water discharge port 474b of the nozzle 473 and the outer circumferential surface 473c of the periphery of the bidet wash water discharge port 474a and the bottom wash water discharge port 474b can be sterilized.

On the other hand, in the second irradiation mode illustrated in FIGS. 9A and 9B, the nozzle 473 is retracted, and the space at the front of the illuminator 650 is open. Then, as in the irradiation area S3 illustrated by the double dot-dash lines of FIGS. 9A and 9B, the sterilizing light is irradiated from the illuminator 650 toward the inner wall 481 of the nozzle storage part 480. Thereby, in the second irradiation mode, the sterilizing light can be irradiated on the inner wall 481 of the nozzle storage part 480, which is in the shadow of the nozzle 473 in the first irradiation mode.

Figure 10A:
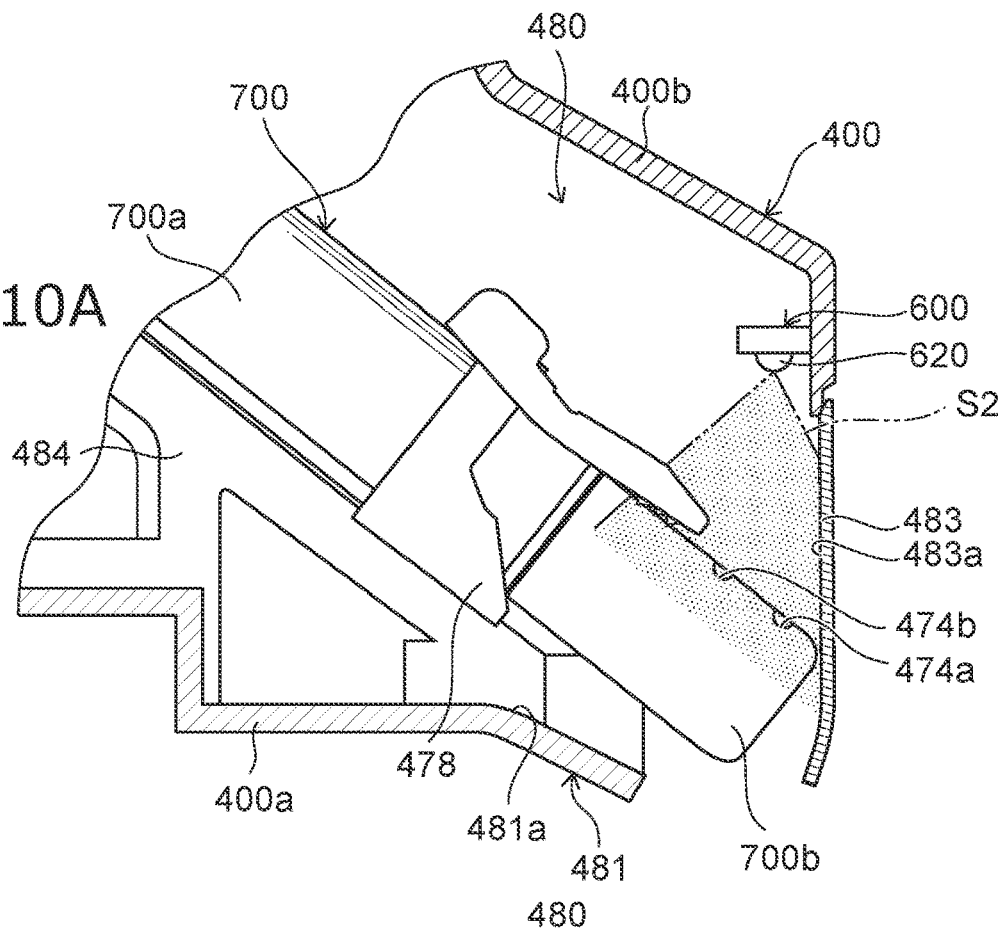
FIGS. 10A and 10B are explanatory drawings illustrating a private part washing nozzle according to a second modification.
Figure 10B:
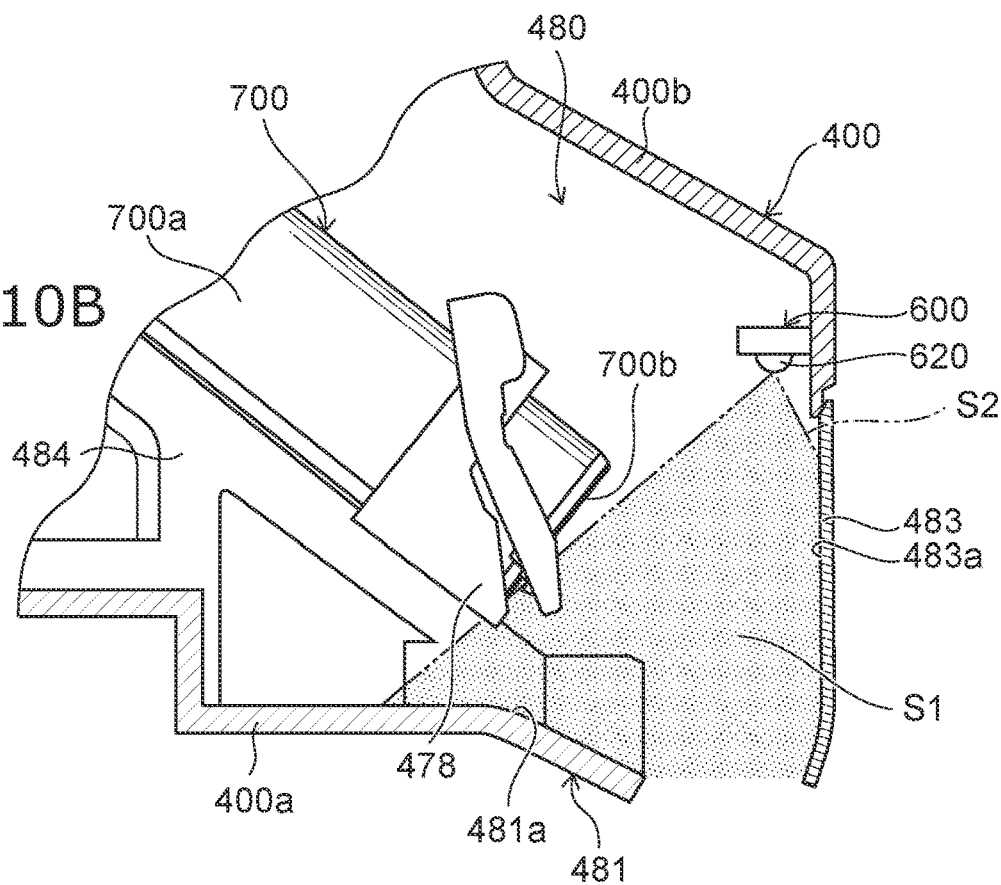

FIGS. 10A and 10B are explanatory drawings illustrating a private part washing nozzle according to a second modification. FIG. 10A is a cross-sectional view of the nozzle and the nozzle storage part in the first irradiation mode when viewed from the side. FIG. 10B is a cross-sectional view of the nozzle and the nozzle storage part in the second irradiation mode when viewed from the side.

An example is described in the embodiment described above in which one nozzle 473 advances and retracts. However, the invention is not limited thereto; for example, as in the second modification illustrated in FIGS. 10A and 10B, a nozzle 700 may have two stages in which an outer tube 700a and an inner tube 700b advance and retract.

An example is described in the embodiment described above in which the first and second irradiation modes are performed by causing the nozzle 473 to advance and retract. However, the invention is not limited thereto; for example, the first irradiation mode and the second irradiation mode may be performed by moving the illuminator. In other words, the illuminator may include a driver. In such a case, the controller may perform the first irradiation mode of irradiating on the outer circumferential surface of the nozzle by causing the driver to move the illuminator, and may perform the second irradiation mode of irradiating on the inner wall of the nozzle storage part by causing the driver to move the illuminator to another position from the first irradiation mode. By such a configuration as well, the first irradiation mode and the second irradiation mode can be performed by the same illuminator.

For example, the following aspects may be considered as sanitary washing devices based on the embodiments described above.

A first aspect includes a private part washing nozzle discharging water toward a private part of a user in a state of the private part washing nozzle being advanced into a toilet, a casing including a nozzle storage part configured to store an entirety of the private part washing nozzle in a state of the private part washing nozzle being retracted, an illuminator irradiating sterilizing light, which has a sterilizing action, into the nozzle storage part, and a controller controlling the illuminator, in which the controller includes a first irradiation mode of causing the sterilizing light irradiated from the illuminator to be irradiated toward an outer circumferential surface of the private part washing nozzle and a second irradiation mode of causing sterilizing light irradiated from the same illuminator as the first irradiation mode to be irradiated toward an inner wall of the nozzle storage part.

According to the first aspect, the sterilizing light can be irradiated on the nozzle storage part and the outer circumferential surface of the private part washing nozzle from the same illuminator. Also, the enlargement of the casing can be suppressed because multiple illuminators for sterilizing both the private part washing nozzle and the nozzle storage part may not be provided.

A second aspect is the first aspect, further including a nozzle driver causing the private part washing nozzle to advance or retract by being controlled by the controller, wherein the controller performs the first and second irradiation modes by causing the nozzle driver to change a position of the private part washing nozzle.

According to the second aspect, the irradiation area of the illuminator can be changed in a state in which the illuminator is fixed. Accordingly, the enlargement of the casing can be suppressed because multiple illuminators for sterilizing both the private part washing nozzle and the nozzle storage part may not be provided.

A third aspect is the second aspect, wherein the illuminator is positioned higher than the private part washing nozzle and is configured to irradiate sterilizing light downward from above; the controller causes the sterilizing light to be irradiated on the outer circumferential surface of the private part washing nozzle by causing the nozzle driver to advance the private part washing nozzle in the first irradiation mode; and the controller causes the sterilizing light to be irradiated on the inner wall of the nozzle storage part by causing the nozzle driver to retract the private part washing nozzle in the second irradiation mode.

According to the third aspect, the sterilizing light can be efficiently irradiated on the outer circumferential surface of the private part washing nozzle and the inner wall of the nozzle storage part.

A fourth aspect is the second or third aspect, wherein the nozzle storage part includes a nozzle lid configured to open and close an opening provided in a front end of the nozzle storage part, and the controller performs the first and second irradiation modes when the nozzle lid is in a closed state.

According to the fourth aspect, leakage outside the nozzle storage part of the sterilizing light irradiated from the illuminator can be suppressed in both the first and second irradiation modes.

A fifth aspect is one of the first to fourth aspects, further including a sterilizing water generator generating sterilizing water for sterilizing the private part washing nozzle, wherein the controller includes a sterilizing water mode using sterilizing water supplied from the sterilizing water generator to sterilize the private part washing nozzle, and the first and second irradiation modes are performed after the sterilizing water mode is performed.

According to the fifth aspect, the sterilizing light can be irradiated on the portions where the residual water of the sterilizing water occurs even when the residual water occurs at the private part washing nozzle and/or the nozzle storage part. Accordingly, the propagation of bacteria and/or mold at the private part washing nozzle and the inner wall of the nozzle storage part can be suppressed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. For example, the shape, the dimension, the material, the disposition, the installation feature or the like of the components included in the sanitary washing device 100 are not limited to the illustration and can be appropriately modified. The components included in the embodiments described above can be combined within the extent of technical feasibility, and any combined components also are included in the scope of the invention to the extent that the feature of the invention is included.

What is claimed is:

1. A sanitary washing device, comprising:
   a private part washing nozzle discharging water toward a private part of a user when the private part washing nozzle is advanced into a toilet;
   a casing including a nozzle storage part configured to store an entirety of the private part washing nozzle when the private part washing nozzle is retracted;

an illuminator irradiating sterilizing light into the nozzle storage part, the sterilizing light having a sterilizing action; and a controller controlling the illuminator, the controller performing
- a first irradiation mode of irradiating sterilizing light from the illuminator toward an outer circumferential surface of the private part washing nozzle, and
- a second irradiation mode of irradiating sterilizing light from the illuminator toward an inner wall of the nozzle storage part.

2. The device according to claim 1, further comprising:

a nozzle driver controlled by the controller to advance or retract the private part washing nozzle, the controller performing the first and second irradiation modes by changing a position of the private part washing nozzle with the nozzle driver.

3. The device according to claim 2, wherein the illuminator is positioned higher than the private part washing nozzle and is configured to irradiate sterilizing light downward from above, and the controller
- advances the private part washing nozzle with the nozzle driver to irradiate the sterilizing light on the outer circumferential surface of the private part washing nozzle in the first irradiation mode, and
- retracts the private part washing nozzle with the nozzle driver to irradiate the sterilizing light on the inner wall of the nozzle storage part in the second irradiation mode.

4. The device according to claim 2, wherein the nozzle storage part includes a nozzle lid configured to open and close an opening provided in a front end of the nozzle storage part, and the controller performs the first and second irradiation modes when the nozzle lid is in a closed state.

5. The device according to claim 1, further comprising:

a sterilizing water generator generating sterilizing water for sterilizing the private part washing nozzle, the controller performing a sterilizing water mode using sterilizing water supplied from the sterilizing water generator to sterilize the private part washing nozzle, the controller performing the first irradiation mode and the second irradiation mode after the controller performs the sterilizing water mode.

\* \* \* \* \*